(12) United States Patent
Bilsbury

(10) Patent No.: US 8,282,572 B2
(45) Date of Patent: Oct. 9, 2012

(54) TISSUE REMOVAL DEVICE

(75) Inventor: Andrew J. Bilsbury, Fairfield, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 225 days.

(21) Appl. No.: 12/818,191

(22) Filed: Jun. 18, 2010

(65) Prior Publication Data

US 2010/0256579 A1    Oct. 7, 2010

Related U.S. Application Data

(63) Continuation of application No. 10/514,143, filed as application No. PCT/US03/19204 on Jun. 17, 2003, now Pat. No. 7,762,959.

(60) Provisional application No. 60/390,024, filed on Jun. 18, 2002.

(51) Int. Cl.
    *A61M 1/00*      (2006.01)

(52) U.S. Cl. ........................................... 600/562

(58) Field of Classification Search ............... 600/562
See application file for complete search history.

(56) References Cited

U.S. PATENT DOCUMENTS

| | | | | |
|---|---|---|---|---|
| 4,947,827 | A | * | 8/1990 | Opie et al. ................... 600/108 |
| 5,037,379 | A | | 8/1991 | Clayman et al. |
| 5,074,867 | A | | 12/1991 | Wilk |
| 5,190,542 | A | * | 3/1993 | Nakao et al. ................... 606/47 |
| 5,201,740 | A | * | 4/1993 | Nakao et al. ................... 606/113 |
| 5,215,521 | A | * | 6/1993 | Cochran et al. ................ 604/22 |
| 5,217,001 | A | * | 6/1993 | Nakao et al. .................. 600/123 |
| 5,354,303 | A | * | 10/1994 | Spaeth et al. ................. 606/128 |
| 5,395,354 | A | * | 3/1995 | Vancaillie ..................... 604/317 |
| 5,423,830 | A | * | 6/1995 | Schneebaum et al. ........ 606/115 |
| 5,465,731 | A | | 11/1995 | Bell et al. |
| 5,480,404 | A | * | 1/1996 | Kammerer et al. ........... 606/113 |
| 5,486,182 | A | * | 1/1996 | Nakao et al. .................. 606/114 |
| 5,486,183 | A | * | 1/1996 | Middleman et al. .......... 606/127 |
| 5,647,372 | A | | 7/1997 | Tovey et al. |
| 5,681,324 | A | * | 10/1997 | Kammerer et al. ........... 606/113 |
| 5,720,754 | A | * | 2/1998 | Middleman et al. .......... 606/127 |
| 5,735,289 | A | * | 4/1998 | Pfeffer et al. ................. 600/564 |
| 5,749,889 | A | * | 5/1998 | Bacich et al. ................. 606/198 |
| 5,759,187 | A | * | 6/1998 | Nakao et al. .................. 606/114 |

(Continued)

FOREIGN PATENT DOCUMENTS

WO    WO 03/105674 A2    12/2003

OTHER PUBLICATIONS

International Application Ser. No. PCT/US03/09133, filed on Jun. 17, 2003; 28 Pages.

*Primary Examiner* — Max Hindenburg
*Assistant Examiner* — Michael C Stout

(57) ABSTRACT

In a tissue removal device for receiving and removing body tissue from an interior portion of a body in a minimally invasive surgical procedure, the tissue removal device including a tubular body having a distal end, a proximal end and defining a lumen therethrough, a bag support structure configured and dimensioned to be receivable within the lumen of the tubular body, wherein the bag support structure has a first configuration for positioning within the lumen of the tubular body and a second configuration for opening a bag operatively coupled thereto, and a bag operatively coupled to the bag support structure, the bag including a first end portion defining an open end.

29 Claims, 10 Drawing Sheets

U.S. PATENT DOCUMENTS

| | | | |
|---|---|---|---|
| 5,800,414 A * | 9/1998 | Cazal | 604/523 |
| 5,908,429 A * | 6/1999 | Yoon | 606/144 |
| 5,944,654 A * | 8/1999 | Crawford | 600/157 |
| 5,997,547 A * | 12/1999 | Nakao et al. | 606/114 |
| 6,004,330 A * | 12/1999 | Middleman et al. | 606/127 |
| 6,007,546 A * | 12/1999 | Snow et al. | 606/113 |
| 6,071,233 A * | 6/2000 | Ishikawa et al. | 600/104 |
| 6,179,776 B1 * | 1/2001 | Adams et al. | 600/121 |
| 6,190,349 B1 * | 2/2001 | Ash et al. | 604/43 |
| 6,352,503 B1 * | 3/2002 | Matsui et al. | 600/104 |
| 6,409,733 B1 * | 6/2002 | Conlon et al. | 606/114 |
| 6,506,166 B1 * | 1/2003 | Hendler et al. | 600/562 |
| 6,527,753 B2 * | 3/2003 | Sekine et al. | 604/264 |
| 6,695,832 B2 * | 2/2004 | Schon et al. | 604/544 |
| 6,740,030 B2 * | 5/2004 | Martone et al. | 600/123 |
| 6,761,685 B2 * | 7/2004 | Adams et al. | 600/121 |
| 6,878,106 B1 * | 4/2005 | Herrmann | 600/104 |
| 6,986,774 B2 * | 1/2006 | Middleman et al. | 606/113 |
| 6,997,931 B2 * | 2/2006 | Sauer et al. | 606/139 |
| 7,029,435 B2 * | 4/2006 | Nakao | 600/153 |
| 7,115,125 B2 * | 10/2006 | Nakao et al. | 606/47 |
| 7,658,738 B2 * | 2/2010 | Nobis et al. | 606/45 |
| 2002/0107530 A1 * | 8/2002 | Sauer et al. | 606/139 |
| 2002/0111534 A1 * | 8/2002 | Suzuki et al. | 600/102 |
| 2003/0130564 A1 * | 7/2003 | Martone et al. | 600/121 |
| 2004/0059314 A1 * | 3/2004 | Schon et al. | 604/544 |
| 2004/0138587 A1 * | 7/2004 | Lyons, IV | 600/562 |
| 2004/0230095 A1 * | 11/2004 | Stefanchik et al. | 600/104 |
| 2004/0230097 A1 * | 11/2004 | Stefanchik et al. | 600/127 |
| 2004/0243175 A1 * | 12/2004 | Don Michael | 606/200 |
| 2005/0096585 A1 * | 5/2005 | Schon et al. | 604/43 |
| 2005/0261674 A1 * | 11/2005 | Nobis et al. | 606/45 |
| 2006/0052799 A1 * | 3/2006 | Middleman et al. | 606/114 |
| 2007/0173687 A1 * | 7/2007 | Shima et al. | 600/106 |

* cited by examiner

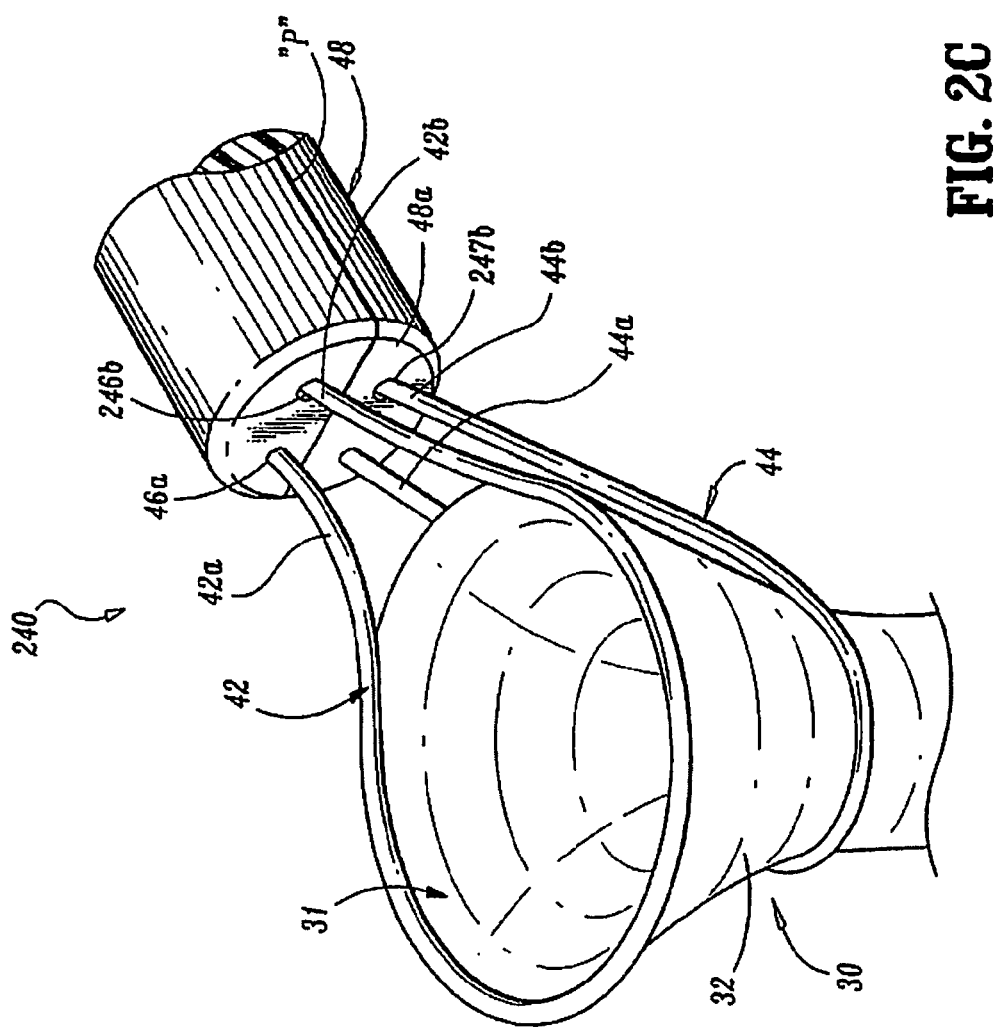

TISSUE REMOVAL DEVICE

CROSS-REFERENCE TO RELATED APPLICATIONS

The present application is a Continuation of U.S. patent application Ser. No. 10/514,143, filed on Nov. 9, 2004, which is a National Stage Application filed under 35 U.S.C. §371(a) of International Application Serial No. PCT/US03/19204, filed on Jun. 17, 2003, which claims the benefit of and priority to U.S. Provisional Patent Application Ser. No. 60/390,024, filed on Jun. 18, 2002, the entire contents of each application being incorporated by reference herein.

BACKGROUND

1. Technical Field

The present disclosure relates to tissue removal devices and, more particularly to tissue removal devices for receiving, retaining and/or removing resected matter from a surgical site.

2. Background of Related Art

Laparoscopic and endoscopic surgical procedures are minimally invasive procedures in which operations are carried out within the body by means of elongated instruments inserted through small entrance openings in the body. The initial opening in the body tissue, to allow passage of the endoscopic or laparoscopic instruments to the interior of the body, may be a natural passageway of the body or may be created by a tissue piercing instrument such as a trocar, a scalpel or a needle.

Endoscopic surgery is popular and commonplace for certain surgical procedures, such as gall bladder removal, ovariectomies and appendectomies. In such procedures, diseased, malignant, necrotic or inflamed tissue and/or organs are excised and removed from the patient. In many endoscopic procedures that involve removal of an organ or tissue such as a gall bladder, appendix, colon, spleen, ovary, lymph node, lung, etc., there is a need for a retrieval bag that can carry and/or contain the organ or portion thereof during its removal from the body cavity in order to reduce the potential for contamination of surrounding tissue and/or organs in the body cavity.

Various apparatus have been devised for introducing, opening, positioning and closing surgical pouches and for removing the pouches and enclosed matter from the surgical site. For example, U.S. Pat. No. 5,037,379 to Clayman et al., the entire contents of which are incorporated herein by reference, discloses a surgical tissue bag. The bag includes a drawstring. In a disclosed method of use, the bag is placed within the body cavity, the body tissue or organ is placed within the bag, the opening of the bag is pulled through the incision in the skin leaving the distal end of the bag containing the tissue or organ within the body cavity, a morcellator is then inserted into the bag, and then the tissue or organ is debulked and suctioned out of the bag.

In U.S. Pat. No. 5,074,867 to Wilk, the entire contents of which are incorporated herein by reference, there is disclosed a membrane having filaments attached to its corners. The membrane is placed within a body cavity with the filaments extending through a cannula to the outside of the body. If the organ and/or tissue is sufficiently deformable, the organ and/or tissue to be removed is placed within the membrane and the filaments are pulled to close the membrane around the organ and/or tissue. The membrane is then removed from the surgical site. If, on the other hand, the organ and/or tissue is not sufficiently deformable, e.g. because of the presence of gall stones, forceps or other instruments are used to crush the stones or tissue prior to withdrawal.

In U.S. Pat. Nos. 5,465,731 to Bell et al. and 5,647,372 to Tovey et al., the entire contents of which are incorporated herein by reference, there is disclosed a specimen retrieval pouch supported by a loop of flexible material. The pouch has a noose retained proximate its open end and is perforated proximate its attachment to the support loop. After the pouch receives its intended contents at the surgical site, it is cinched closed by pulling upon a suture leading to the noose. Cinching the pouch closed aids the separation of the pouch from the support loop via tearing along the perforation line. Once the pouch has been torn from the expanded loop pouch support, the support may be retracted and the instrument withdrawn.

Although retrieval bags such as those described above are known, there remains a need for improved specimen retrieval pouches to facilitate tissue removal in minimally invasive surgical procedures. There remains a need for specimen retrieval pouches that minimize the wound at the exit site for removing the pouch after the pouch has received tissue.

SUMMARY

The present disclosure relates to tissue removal devices for receiving, retaining and/or removing resected matter (e.g., body tissue and/or body organs) from a surgical site.

According to one aspect of the present disclosure, a tissue removal device includes a tubular body having a distal end, a proximal end and defining a lumen at least partially therethrough, and a bag support structure configured and dimensioned to be receivable within the lumen of the tubular body. The bag support structure has a first configuration for positioning within the lumen of the tubular body and a second configuration for opening a bag operatively coupled thereto. The device further includes a bag operatively coupled to the bag support structure, the bag including a first end portion defining an open end, a mid-portion, and a second end portion opposite the first end portion. The bag support structure includes a first member disposed between the first end portion and the second end portion for at least partially closing the bag. The first member may be used to manipulate tissue while disposing the tissue in the bag.

In certain preferred embodiments, the bag support structure includes a shaft extending through the lumen of the tubular body, the shaft including a distal end and a proximal end. The first member is desirably slidably received in the shaft. The bag support structure preferably includes a second member disposed at the first end portion of the bag. The first member may be used to engage tissue and to position tissue while the second member is used to close the open end of the bag. The device may be used in various procedures and may be used to position a first length of tissue within the bag, closing the first member, and the positioning a second length of tissue in the bag and closing the second member.

It is envisioned that the first member includes a first hoop translatably received in the shaft and the second member includes a second hoop translatably received in the shaft. The first hoop is desirably spaced from the second hoop in the longitudinal direction of the bag.

Each of the first and second members desirably has a first position in which the bag is substantially closed and a second position in which the bag is substantially open. Each of the first and second members is desirably made of a flexible member extending through at least one aperture formed in the distal end of the shaft.

It is envisioned that displacement of the first and second members in a distal direction urges the respective one of the first and second members to the second position. It is further envisioned that displacement of the first and second members, in a proximal direction, urges the respective one of the first and second members to the first position.

In certain embodiments, each of the first and second members has a first end secured to the distal end of the shaft and a second end extending through the distal end of the shaft. Accordingly, displacement of the second end of each of the first and second members, in a proximal and distal direction, urges the first and second members between the first and second position.

In certain embodiments, the first member of the bag support structure includes a ring, and a rod operatively connected to the ring. The bag support structure further includes a hoop disposed at the first end portion of the bag. The frame is spaced a transverse distance from the hoop.

The first member is desirably made of a deformable material. Preferably, the first member is biased to a second position in which the bag is substantially open. The deformable material can be any one of stainless steel, titanium, a composite material, a shape memory alloy and plastic.

The bag desirably has a generally elongate shape. In certain embodiments, the bag has a mid-portion with a generally elongate shape. The mid-portion of the bag desirably has a first diameter and the first end portion of the bag desirably has a second diameter which is greater than the first diameter of the mid-portion.

The tissue removal device further preferably includes a removable sheath for encasing the bag and at least a portion of the bag support structure therein.

In certain embodiments, the tissue removal device further includes a plurality of ribs extending longitudinally along a length of the bag.

The tissue removal device may further include a grasper operatively coupled to a distal end of the bag support structure.

In one embodiment, the first member includes a first hoop operatively connected to the first end portion of the bag, and wherein a second member includes a second hoop operatively connected to the bag at a location spaced a distance from the first end portion. Each of the first and second hoops has a first configuration in which the bag is substantially closed and a second configuration in which the bag is substantially open.

Each of the first and second hoops may be made of a wire extending through at least one aperture formed in the distal end of the shaft. Accordingly, displacement of the wire of each of the first and second hoops, in a distal direction, urges the respective one of the first and second hoops to the second configuration. Moreover, displacement of the wire of each of the first and second hoops, in a proximal direction, urges the respective one of the first and second hoops to the first configuration.

In another embodiment, the first member includes a ring operatively connected to a distal end of a rod. The ring is also operatively connected to the first end portion of the bag, and wherein the hoop is operatively connected to the bag at a location spaced a distance from the first end portion of the bag.

The ring is desirably resilient. The ring has a first configuration in which the ring is biased for receipt in the lumen of the tubular body and a second configuration in which the ring is unbiased and has a diameter larger than the diameter of the lumen of the tubular body.

It is envisioned that a mid-portion of the bag has a first diameter and the first end portion of the bag has a second diameter which is greater than the first diameter of the mid-portion.

The tissue removal device can further include a removable sheath for encasing the bag and the distal end of the bag support structure therein.

The tissue removal device can further include a plurality of ribs extending longitudinally along a length of the bag.

The present disclosure is also related to a method of removing body tissue from an interior portion of a body in a minimally invasive surgical procedure. The method includes the step of introducing a tissue removal device into the body, wherein the tissue removal device includes a bag support structure and a bag operatively connected to the bag support structure, the bag support structure including a first member disposed between a first end portion and a second end portion of the bag for at least partially closing the bag.

The method further includes the steps of deploying the bag from a first configuration to a second configuration in which the bag is substantially open, introducing body tissue into the bag, and manipulating the first member so as to at least partially close the bag.

In certain embodiments, the step of manipulating the first member includes engaging the body tissue. The bag support structure preferably includes a second member at the first end portion of the bag, and the method preferably includes manipulating the second member to at least partially close the bag. In certain preferred embodiments, the device is used to position a first length of tissue in the bag, close the first member and then position a second length of tissue in the bag and close the second member.

These and other advantages and features of the present apparatus disclosed herein, will become apparent through reference to the following description of embodiments, the accompanying drawings and the claims.

BRIEF DESCRIPTION OF THE DRAWINGS

By way of example only, preferred embodiments of the present disclosure will be described herein with reference to the accompanying drawings, in which:

FIG. 2C is an enlarged perspective view of a distal end of a tissue removal device according to yet another embodiment of the present disclosure, wherein one end of the first and/or second hoop is movable;

DETAILED DESCRIPTION OF PREFERRED EMBODIMENTS

Figure 1:
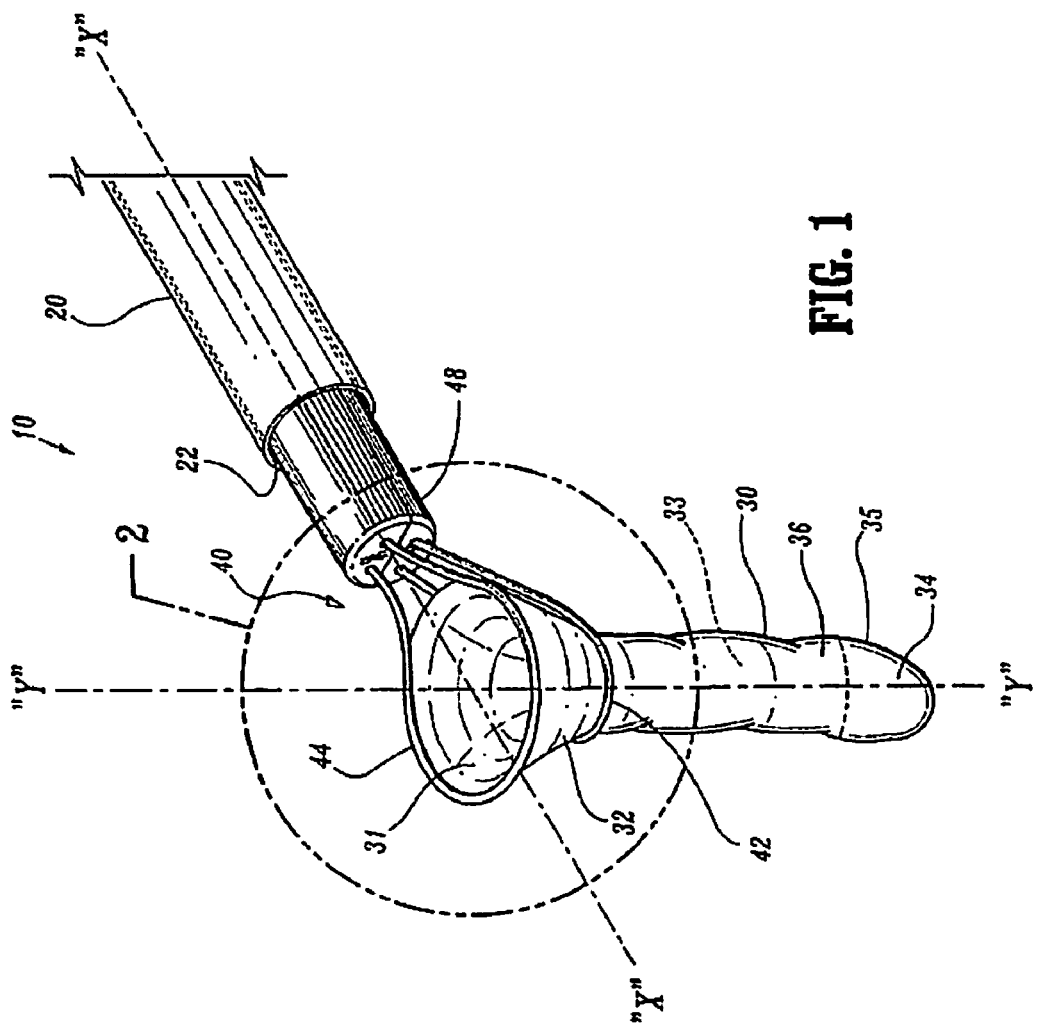
FIG. 1 is a perspective view of a distal end of a tissue removal device in accordance with one embodiment of the present disclosure, shown in a second or opened deployed condition.

Preferred embodiments of a presently disclosed tissue removal device will now be described in detail with reference to the drawing figures wherein like reference numerals identify similar or identical elements. In the drawings and in the description which follows, the term "proximal", as is traditional will refer to the end of the surgical device or instrument of the present disclosure which is closest to the operator, while the term "distal" will refer to the end of the device or instrument which is furthest from the operator.

One embodiment of a tissue removal device, in accordance with the present disclosure, is shown in FIGS. 1, 2A and 3-8. Tissue removal device 10 includes an endoscopic shaft or tubular body 20 having a lumen 22 extending therethrough and defining a longitudinal axis "X". Tissue removal device 10 further includes a bag support structure 40 having a bag 30 operatively connected thereto. Desirably, bag support structure 40 is receivable in lumen 22 of tubular body 20. Bag support structure 40 may comprise any openable structure. Bag 30 may be connected to bag support structure 40 by a variety of known means such as the upper end of bag 30 being configured to receive bag support structure 40. Bag 30 comprises a flexible film or sheet and may comprise a substantially transparent polymeric material. Polyurethane, latex and any other bio-compatible material may be used. Bag 30 has dimensions suitable for entrapping and/or removing tissue.

Bag 30 has a first end portion 32 defining an opening 31. Bag 30 also has a second end portion 34 defining a closed end 35 opposite the first end portion 32 and a mid-portion 36 between the first end portion 32 and second end portion 34. It is contemplated that tubular member 20 can be a rigid or a flexible member. Tubular body 20 has an outside diameter configured for passage through a cannula 90 (see FIG. 4).

Figure 2A:
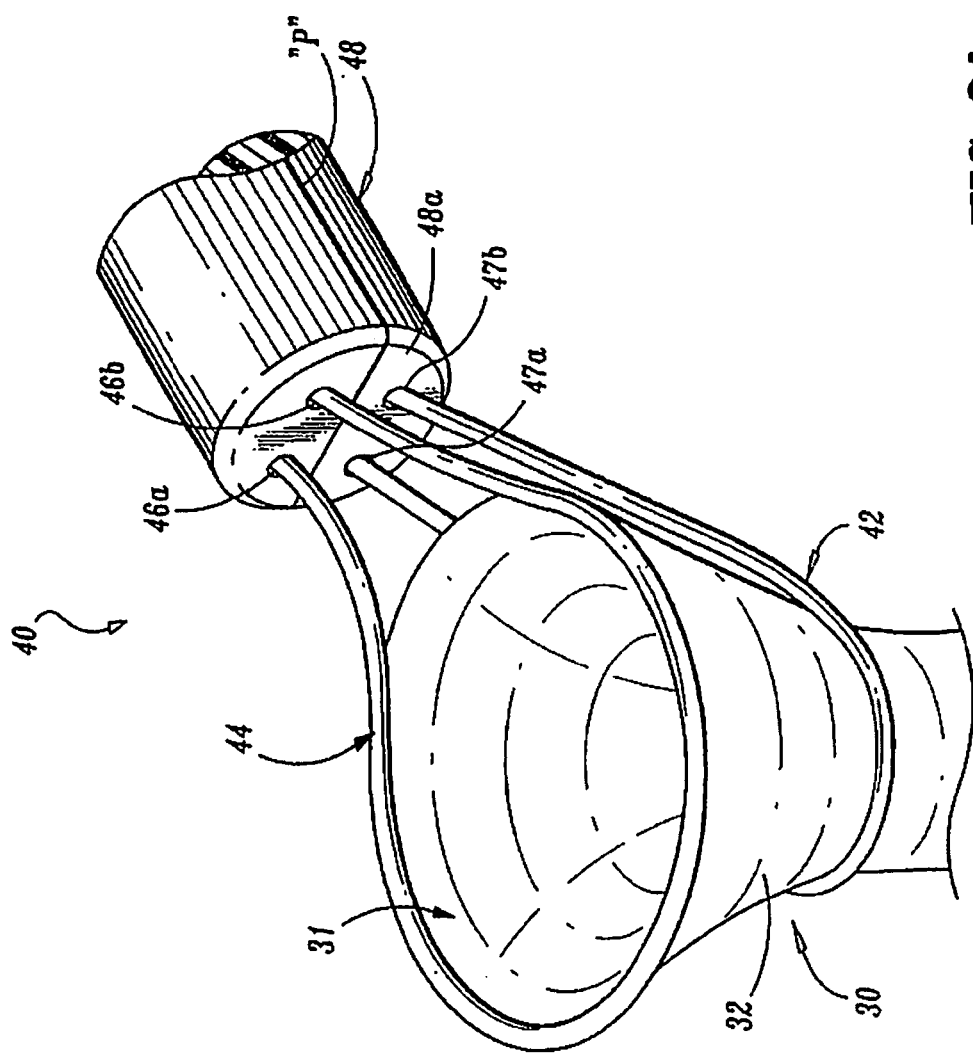
FIG. 2A is an enlarged perspective view of the tissue removal device of FIG. 1.
Figure 3:
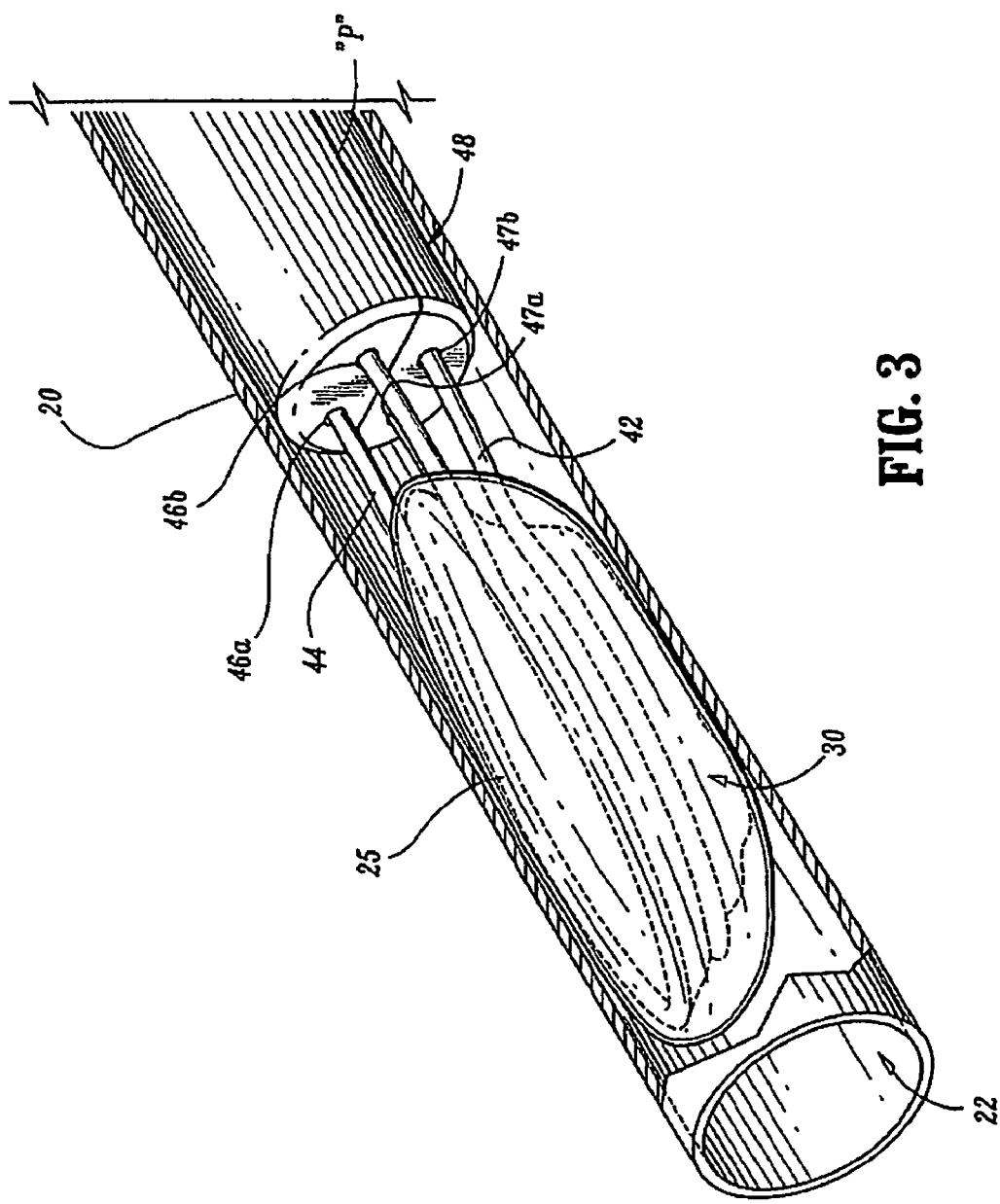
FIG. 3 is an enlarged perspective view of the tissue removal device of FIGS. 1 and 2A shown in a first or closed/folded condition.

As best seen in FIGS. 1, 2A and 3, bag support structure 40 includes an elongate shaft 48 having a distal end 48a and a proximal end 48b. It is envisioned that support structure 40 is configured and adapted to be directed or manipulated by a surgeon using a control portion 60 (see FIG. 6). Bag support structure 40 further includes a first member 42 operatively associated with distal end 48a of shaft 48 and a second member 44 operatively associated with distal end 48a of shaft 48 and spaced a longitudinal distance along a transverse axis "Y" from first member 42. Desirably, first member 42 is translatably received in and/or exits distal end 48a of shaft 48 through a pair of apertures 47a, 47b formed therein, and forms a hoop. In addition, second member 44 is desirably translatably received in and/or exits distal end 48a through a pair of apertures 46a, 46b formed in distal end 48a and forms a hoop. While a pair of apertures 46a, 46b and 47a, 47b are provided for each of first member 42 and second member 44, it is envisioned that each member 42, 44 can exit a respective aperture formed in distal end 48a of shaft 48 or both hoops 42, 44 exit a common aperture formed in distal end 48a of shaft 48.

First member 42 is preferably formed of a relatively flexible wire or band which exits aperture 47a and enters aperture 47b of shaft 48. Desirably, the wire of first member 42 extends proximally through shaft 48 and enables the surgeon to adjust and control the dimensions of first member 42, preferably from control portion 60. First member 42 is operatively connected between the junction between first end portion 32 and mid-portion 36 of bag 30. An adjustable first member 42 has the advantage that the diametral size of the hoop can be reduced while tissue removal device 10 is being inserted through cannula 90 and can thereafter be expanded remotely after insertion into the body cavity. Further, as will be discussed in greater detail below, an adjustable first member 42 permits closure of bag 30 after the resected body tissue has been placed therein and for the withdrawal of tissue removal device 10 back through cannula 90.

Second member 44 is also preferably formed by a relatively flexible wire or band and, as will be described in greater detail below, is preferably operatively connected to first end portion 33 of bag 30. Desirably, the wire of second member 44 extends proximally through shaft 48 and enables the surgeon to adjust and control the dimension of second member 42 from control portion 60, thereby selectively opening and closing interior 33 of bag 30. Second member 44 can also be reduced in diameter for insertion through a cannula and for closing the bag. As will be discussed in greater detail below, first member 42 may be used to assist in the loading of resected body tissue portions into bag 30 by temporarily holding at least a portion of the resected body tissue while the remaining portion of the resected body tissue is positioned through opening 31 during the loading sequence of bag 30. Preferably, first member 42 is configured and adapted to be independently adjusted with respect to second member 44, however, it is envisioned that first member 42 can be adjusted simultaneously with second member 44.

First and second members 42, 44 are preferably fabricated from a wire or band of material capable of providing structural support for as well as being capable of being connected to bag 30. First and second members 42, 44 are preferably made of a suitable medical grade metal, composite or plastic material having the required structural integrity to provide support and flexibility for deforming when being inserted through the cannula into the body cavity and the required rigidity to enable enlargement of opening 31 of bag 30 after deployment of tissue removal device 10. First and second members 42, 44 are desirably comprised of any flexible and/or resilient material and are preferably biased to an open position. Preferably, first and second members 42, 44 are maintained within the tubular body 20, in a closed position. In the closed position, second member 44 closes opening 31. First member 42 closes around bag 30, between first end portion 32 and mid portion 36. It is contemplated that first and second members 42, 44 can be formed from shape memory alloys, assuming predefined shapes, such as, for example, quadrangular, circular or other geometric two-dimensional or three-dimensional configurations.

Figure 2B:
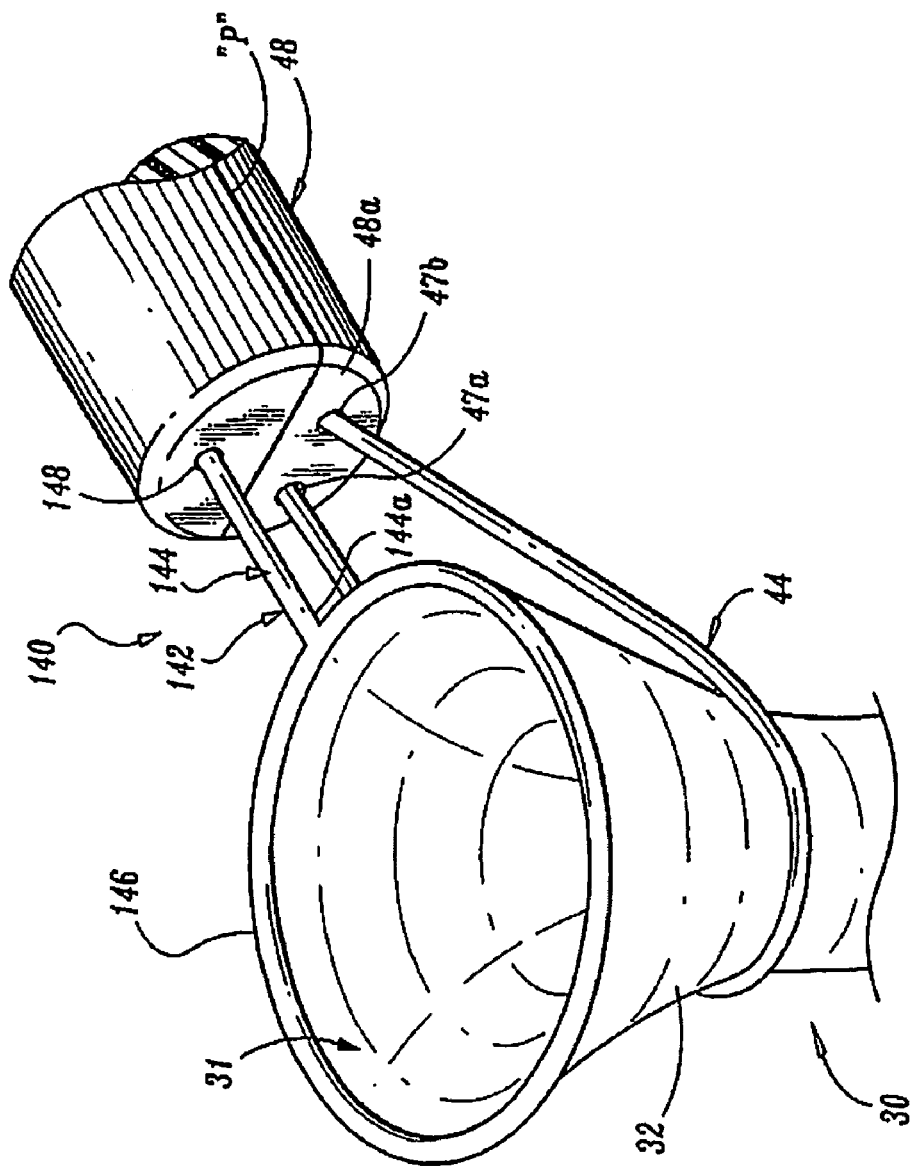
FIG. 2B is an enlarged perspective view of a distal end of a tissue removal device according to another embodiment of the present disclosure.

Turning now to FIG. 2B, an alternate embodiment of a bag support structure is shown generally as 140. Bag support structure 140 is similar to bag support structure 40 and will only be discussed in detail to the extent necessary to identify differences in construction and operation.

As seen in FIG. 2B, first member 42 has been replaced with a frame 142 having an elongate rod 144 having a distal end 144a and a ring 146 operatively connected to distal end 144a of rod 144. Desirably, rod 144 is translatably received in shaft 48 such that a distal end of rod 144 exits distal end 48a of shaft 48 through an aperture 148 formed therein and a proximal end of rod 144 extends proximally through shaft 48 and enables the surgeon to position and control ring 146. Ring 146 is operatively connected to first end portion 32 of bag 30.

Ring 146 is preferably fabricated from a wire or band of other material capable of supporting bag 30. Ring 146 is made of a suitable medical grade metal, composite or plastic material having the required structural integrity to provide support, as well as flexibility for deforming for being positioned in lumen 22 of tubular body 20. Ring 146 should have sufficient rigidity to enlarge and open opening 31 of bag 30 after deployment of tissue removal device 10. It is contemplated that ring 146 can be formed from shape memory alloys, assuming predefined shapes, such as, for example, quadrangular, circular or other geometric two-dimensional or three-dimensional configurations.

Turning now to FIG. 2C, an alternate embodiment of a bag support structure is shown generally as 240. Bag support structure 240 is similar to bag support structure 40 and will only be discussed in detail to the extent necessary to identify differences in construction and operation.

As seen in FIG. 2C, first member 42 has a first end 42a fixedly secured to distal end 48a of shaft 48 and a second end 42b which is translatably received in and/or extends through an aperture 246b formed therein. In addition, second member 44 has a first end 44a fixedly secured to distal end 48a of shaft 48 and a second end 44b which is translatably received in and/or extends through an aperture 247b formed therein. Desirably, second ends 42b, 44b of first and second members 42, 44 extend through shaft 48 to a proximal end thereof. In this manner, the surgeon can move second ends 42b, 44b in a proximal or distal direction to enlarge and/or constrict the size of first and second members 42, 44 as needed.

Figure 5:
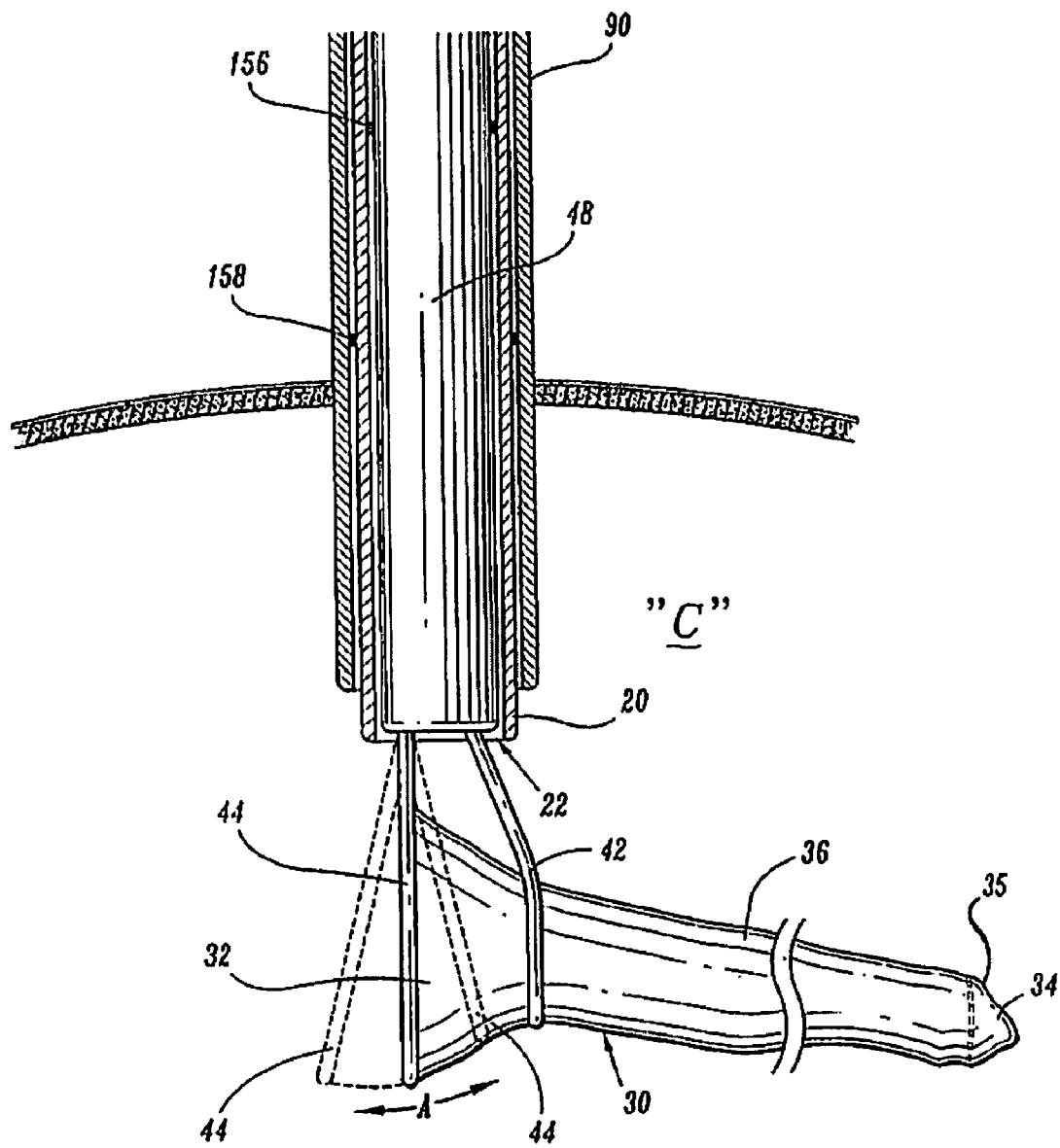
FIG. 5 is a side elevational view of the tissue removal device of FIGS. 1, 2A, 3 and 4, in a second or deployed condition, in the body cavity.

Bag 30 and bag support structure 40 have a first, pre-deployed condition, as shown in FIG. 3, and a second, deployed condition as shown in FIGS. 1 and 5. As seen in FIGS. 1 and 5, bag 30 defines an interior 33 extending from the opening 31 to the closed end 35 when in the deployed condition. In accordance with the present embodiment, first end portion 32 preferably has a conical or tapered shape that transitions from opening 31 to mid-portion 36. Accordingly, opening 31 has a larger diameter than interior 33, in mid-portion 36, wherein first end portion 32 is a chute-like opening which facilitates the introduction of portions of body tissue and/or organs through opening 31 of first end portion 32 and mid-portion 36. It is contemplated that while in the deployed condition, first end portion 32 and mid-portion 36 are centrally aligned along an axis "Y". Although bag 30 is shown with a closed end 35, a tapered first end portion 32 and an enlarged mid-portion 36, bag 30 may comprise other shapes.

Bag 30 is configured and adapted for the positioning, retention and withdrawal of portions of body tissue and/or organs, such as, for example, a resected portion of a colon, through cannula 90. In general, the dimensions of a tissue removal bag, carrying tissue for removal through a cannula, is limited by the inside diameter of the cannula. As such, quantities of resected portions of body tissue and/or organs which cause the bag to expand to a dimension which is greater than the diameter of the cannula can not be placed within the bag and can not be removed in a single step. Accordingly, it is contemplated that bag 30 be provided with an extended or elongated mid-portion 36 thus allowing for a greater quantity of resected portions of body tissue and/or organs to be contained within bag 30 and distributed along the longitudinal axis "Y" of bag 30, so that a greater quantity of tissue can be removed from the body cavity in a single step. In other words, the tissue and/or organ can be positioned for removal from the body via a relatively smaller exit wound. Preferably, bag 30 has suitable strength and flexibility in order to be withdrawn through the cannula while still retaining its load of resected tissue material. It is further contemplated that bag 30 can be configured with folds, pressure vessel releases or secondary passageways to ensure that air will not be trapped in lumen 33 of bag 30 as body tissue and/or organs are placed therein.

Preferably, bag 30 is made from a flexible film or sheet formed from a substantially transparent polymeric material. In one preferred embodiment, bag 30 is fabricated from polyurethane having a thickness of about 0.001 to about 0.005 inches. It is envisioned that other appropriate biocompatible materials capable of forming a flexible membrane, such as, for example, latex, having other appropriate thicknesses, may be used as well. In certain preferred embodiments, the material of bag 30 is transparent to permit viewing of its contents. In addition, the material should be selected such that bag 30 is impervious to penetration, seepage or leaking of cells or any material therethrough.

Desirably, device 10 has a control portion 60 for relative manipulation of shaft 48, tubular body 20 and hoops 42, 44.

In the pre-deployed condition, as seen in FIG. 3, it is envisioned that bag 30 and support structure 40 may be at least partially encapsulated by a sheath 25 which is configured and adapted to be removed after passage of bag 30 and support structure 40 through lumen 22 of tubular body 20. In certain embodiments, bag 30 is folded or rolled into a shape minimizing its dimensions prior to sheath 25 being placed therearound. For example, bag 30 has at least one transverse fold, as disclosed in certain embodiments of International Application No. PCT/US03/09133, filed Mar. 21, 2003, the disclosure of which is hereby incorporated by reference herein. It is contemplated that bag 30 and support structure 40 can be minimized with the aid of mechanical or pneumatic (e.g., vacuum) means for reducing the volume of bag 30 and the dimensions of support structure 40. After bag 30 and support structure 40 have been minimized, sheath 25 is slipped over bag 30 and supporting structure 40 such that bag 30 and supporting structure 40 retain their minimized configurations. In this manner, as seen in FIG. 3, bag 30 and supporting structure 40 are sized and dimensioned to be received in lumen 22 of tubular body 20. Preferably, device 10 is provided with the collapsed and minimized bag 30 and bag support structure 40 housed in the lumen 22, prior to use.

In use, first member 42 can be rotated about longitudinal axis "X" by rotating elongate shaft 48 about the "X" axis. It is desirable that first member 42 is bendable, in the directions indicated by double-headed arrow "A" in FIG. 5, relative to shaft 48. The bendability of second member 44 enables positioning and orientation of second member 44 in plane X-Y. Bag support structure 40 is further positioned by rotating shaft 48 so that second member 44 is positioned and oriented in planes transverse to the X-Y plane. The bendable second member 44 advantageously allows positioning of first member 42 for greater control of supporting structure 40 to capture resected body tissue and/or organs into bag 30. Shaft 48 is made of suitable medical grade metals, composites or plastics having the required structural integrity and flexibility for positioning and withdrawing of bag 30 through cannula 90.

Referring now to FIGS. 4-8, the use of tissue removal device 10 will be described. Bag supporting structure 40 and bag 30 are disposed in the first pre-deployed condition. Tissue removal device 10 is introduced into body cavity "C" via tubular body 20 received in the cannula 90. After tissue removal device 10 has been introduced into body cavity "C", sheath 25 is removed to thereby expose and/or release bag 30 and bag support structure 40.

With bag 30 and bag support structure 40 released, tissue removal device 10 can be manipulated from the first pre-deployed condition to the second deployed condition. Shaft 48 is extended so that first and second members 42, 44 are exposed. As first and second members 42, 44 are biased to the open position, bag 30 is opened upon release from tubular body 20. Bag 30 unrolls and extends away from first and second members 42, 44. In the second condition, tissue retrieval device 10 is ready to receive portions of resected body tissue and/or organs therein. While in the second condition, first member 42 can be expanded and/or contracted by moving the wires or bands of first member 42 in a distal and proximal direction to thereby open and/or close opening 31 of bag 30. In addition, second member 44 can be expanded and/or contracted by moving the wires or bands of second member 44 in a distal and a proximal direction to thereby open and/or close mid-portion 36 of bag 30. First and second members 42, 44 may be further moved in the distal and proximal directions to position bag 30 and ease the capture of tissue within bag 30. First and second members 42, 44 may be manipulated individually or together.

Figure 6:
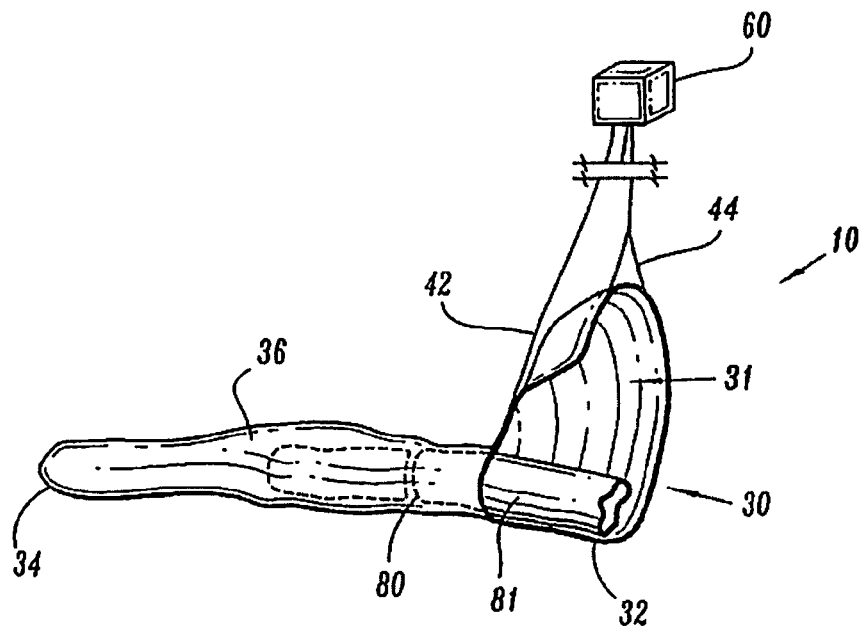
FIG. 6 is a schematic side elevational view, partially broken away, of the tissue removal device of FIGS. 1, 2A and 3-5, at a stage in a method of the present disclosure, illustrating positioning of body tissue and/or organs into the bag.
Figure 7:
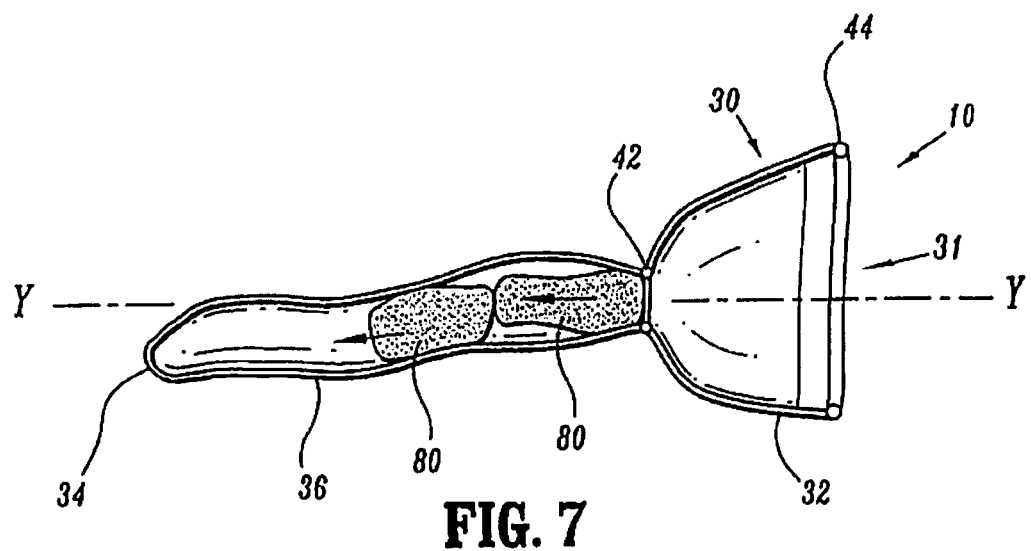
FIG. 7 is a schematic cross-sectional side elevational view of the tissue removal device of FIGS. 1, 2A and 3-6, shown at a later stage of the method of the present disclosure, illustrating the removed body tissue and/or organ contained in the bag.

An illustrative example of the placement of resected portions of body tissue and/or organs into bag 30 of tissue removal device will now be described with reference to FIGS. 6 and 7. Once resected body tissue, such as, but not limited to a resected colon 80, is introduced into bag 30 and into mid-portion 36, first member 42 is retracted to hold a portion of resected colon 80, while the remaining portion of resected colon 80 is positioned through opening 31 of bag 30. In addition, with a portion of resected colon 80 being held in place against movement by cinched first member 42, the remaining portion 81 of resected colon 80 can be properly oriented and held in place during its removal from the surrounding body. With the remaining portion 81 of resected colon 80 removed from the surrounding body, the remaining portion 81 of resected colon 80 is placed in first end portion 32 of bag 30. First member 42 is then expanded so that the remaining portion 81 of resected colon 80, retained in first end portion 32, can be fully received into mid-portion 36. For larger pieces of resected body tissue, this process can be repeated as many times as necessary until the entire resected colon 80 is retained in mid-portion 36 of bag 30. In order to maximize the use of bag 30, resected colon 80 is advanced through interior 33 until it is positioned near second end portion 34 of bag 30.

It is envisioned that this process can also be assisted with the aid of a grasper 70 (see FIG. 9) operatively coupled to a distal end of tubular body 20, or with a separate grasper configured and adapted to operate in cooperation with tissue removal device 10, or with a conventional grasper.

Figure 8:
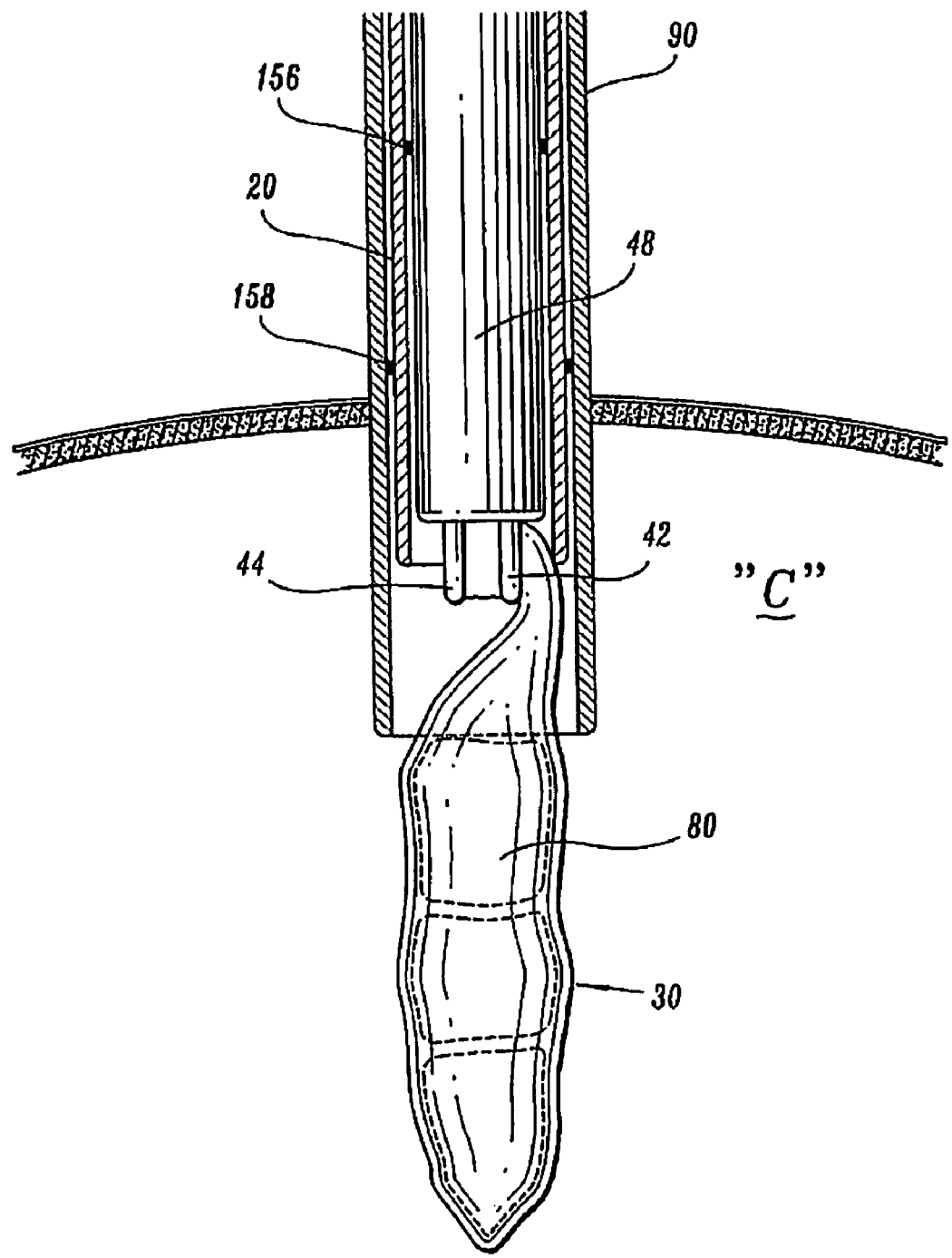
FIG. 8 is a cross-sectional side elevational view of the tissue removal device of FIGS. 1, 2A and 3-7, shown in a later stage of the method of the present disclosure, illustrating withdrawal of the tissue removal device, containing body tissue and/or organs, from the body cavity.

As seen in FIG. 8, when bag 30 is fully loaded or when all of the desired portions of resected body tissue and/or organs to be removed have been loaded into bag 30, first and second members 42, 44 are withdrawn, either individually or together, from control portion 60 to reduce the operable diameters of members 42 and 44. In other words, first member 42 is cinched in order to prevent the escape of portions of resected colon 80 from within bag 30 and to reduce the diameter of first member 42 in order to enable the withdrawal of bag support structure 40 through tubular body 20. Meanwhile second member 44 is cinched to reduce its diameter in order to enable its withdrawal through tubular body 20 as well as to provide a second closure to bag 30 to ensure that the portions of resected colon 80 do not inadvertently or accidentally escape from bag 30.

In use, sheath 25 may be removed after deploying bag 30 and support structure 40 from tubular body 20.

While a first member 42 and a second member 44 have been disclosed, it is envisioned that any number of members can be provided along the longitudinal length of bag 30. Accordingly, bag 30 can be of any three dimensional configuration, including but not limited to cylindrical, spherical, rectangular, cubical, etc. Each of these configurations can be achieved by placing an expandable member at a pre-selected location along the length of bag 30 and then expanding the member according to the desired shape and configuration required. While many shapes are possible, it is preferable that bag 30 have a substantially elongated cylindrical configuration (e.g., in the form of a sausage bag) in order for bag 30 to be most easily withdrawn through tubular body 20 after bag 30 has been filled.

Figure 4:
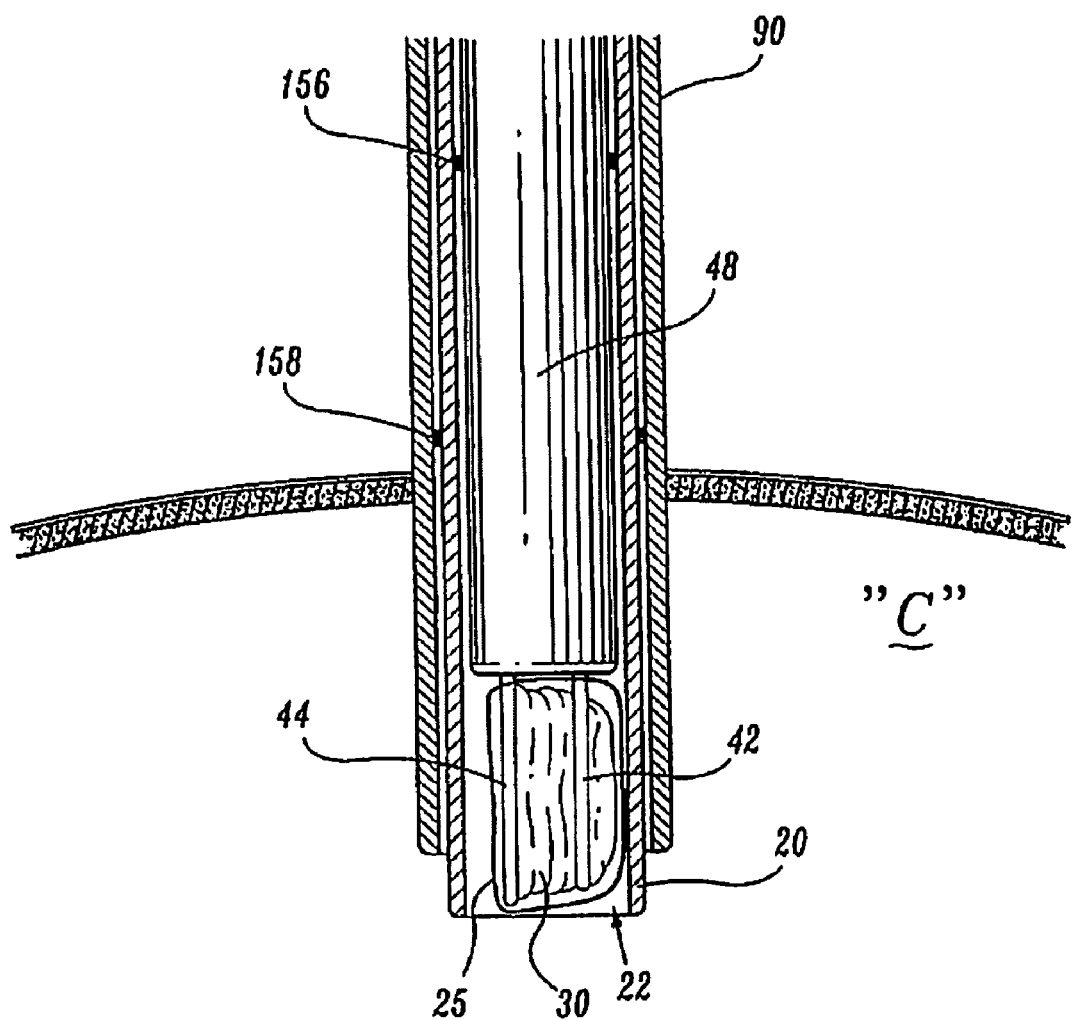
FIG. 4 is a cross-sectional side elevational view of the tissue removal device of FIGS. 1, 2A and 3 as it is inserted into a body cavity through a cannula.

It is further contemplated that the elongate shaft of the tissue removal device be provided with circumferential slots (not shown) formed along the inner surface thereof for receiving O-ring type seals 156 (see FIGS. 4, 5 and 8). O-rings 156 help to maintain a gaseous seal while permitting sliding movement of elongate shaft 48 through tubular body 20. Similarly, it is envisioned that tubular body 20 be provided with circumferential slots (not shown) formed along the outer surface thereof for receiving additional O-ring type seals 158. O-rings 158 help to maintain a gaseous seal while permitting sliding movement of tubular body 20 through cannula 90.

As seen in FIGS. 2A, 2B, 2C and 3, the elongate shaft 48 is longitudinally divided along a plane "P" to define a first-half shaft portion 49a and a second-half shaft portion 49b. It is envisioned that first-half shaft portion 49a and second-half shaft portion 49b can be configured and adapted to be separated from one another and interchanged and/or replaced with other half sections which provide the surgeon with an operative end as desired. For example, half sections including support structures 40 (FIG. 2A), 140 (FIG. 2B) and/or 240 (FIG. 2C) as well as graspers 70 can be combined with and/or interchanged with one another to perform certain functions desired by the surgeon during the surgical procedure. In other embodiments, the shaft 48 comprises a single unitary shaft.

Figure 9:
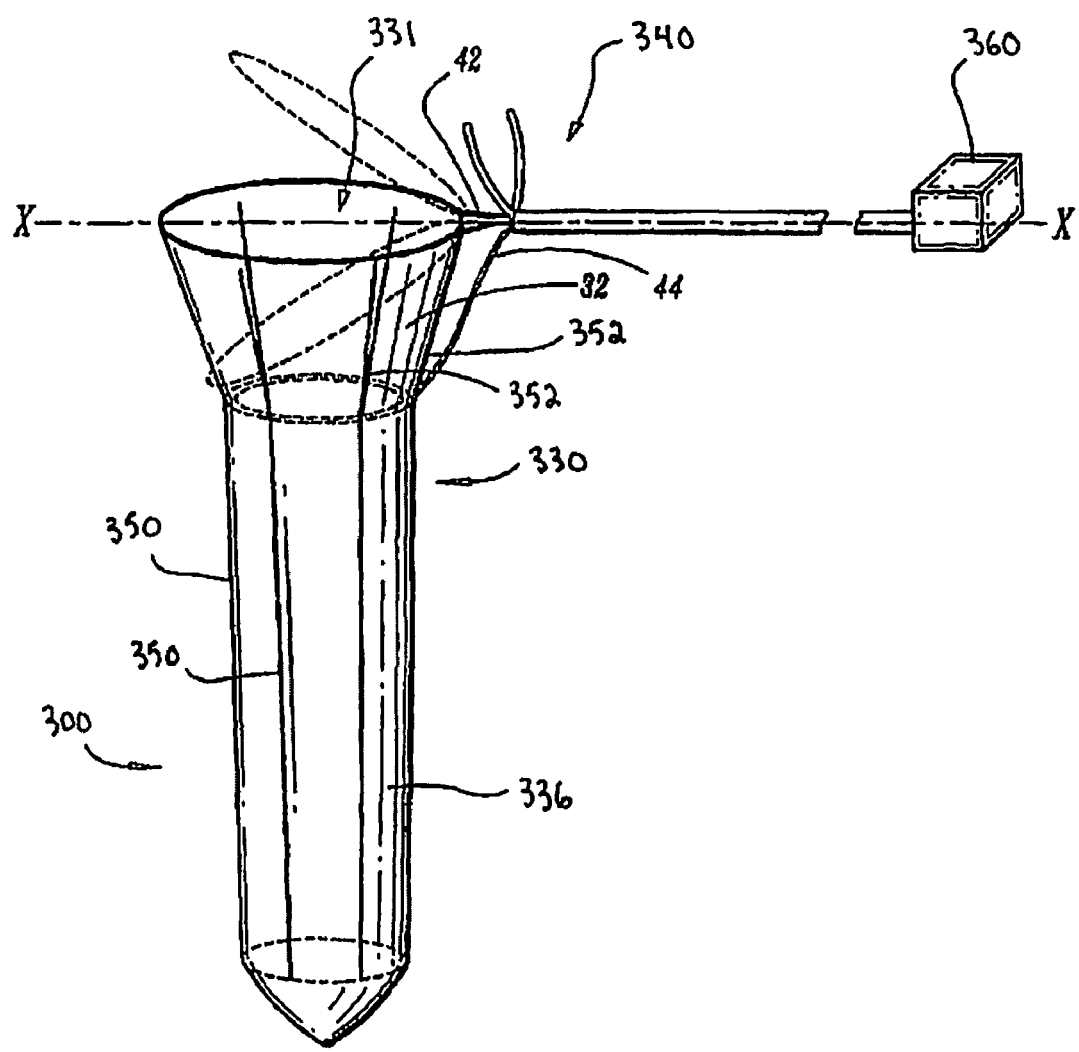
FIG. 9 is a perspective view of a tissue removal device in accordance with an alternative embodiment of the present disclosure.

Referring now to FIG. 9, an alternative embodiment of a tissue removal device, in accordance with the present disclosure, is shown generally as 300. Tissue removal device 300 is similar to tissue removal device 10 and will only be discussed in detail to the extend necessary to identify differences in construction and operation As seen in FIG. 9, bag 330 of tissue removal device 300 includes a plurality of ribs 350 operatively associated (e.g., woven into, glued onto, etc.) around the circumference of mid-portion 336 of bag 330. Desirably, when bag support structure 340 is in the second condition, as seen in FIG. 9, ribs 350 extend substantially in the direction of axis "Y". Bag 330 can further include a plurality of ribs 352 operatively associated around the circumference of first end portion 32 of bag 330. Desirably, ribs 352 extend substantially between opening 331 and mid-portion 336 of bag 330.

Ribs 350 and 352 provide bag 330 with shape and definition when tissue removal device 300 is in the second, deployed condition. In other words, when in the second deployed condition, ribs 350, 352 assist bag 330 in extending/expanding to its full dimensions.

Ribs 350, 352 are fabricated from a wire or band and is configured and adapted to provide structural support for bag 330. The wire stock is made of a suitable medical grade metal, composite or plastic material having the required structural integrity to provide support and flexibility for deforming when being inserted through the cannula into the body cavity as well as the required rigidity to enable remote enlargement of bag 330 to its full dimensions after deployment of tissue removal device 300.

It is envisioned that a fiber optic viewing system (not shown) is employed in conjunction with the supporting structure. It is contemplated that the fiber optic viewing system be operatively coupled to the control portion 360 such that the fiber optic viewing system moves together with a movement of the first member 42 and/or second member 44.

Although illustrative embodiments of the present disclosure have been described herein, it is understood that the disclosure is not limited to those precise embodiments, and that various other changes and modifications may be affected therein by one skilled in the art without departing from the scope or spirit of the disclosure. For example, the sheath for containing the bag and support structure may be omitted or may be provided in the form of a housing or container. The bag may be advanced from the lumen of the tubular body prior to removing the sheath, and the bag may be deployed upon removal of the sheath or release from the lumen, or both. In certain embodiments, the tubular body may be omitted and the hoops may be deployed from openings in the shaft. The hoops may be deployed upon removal of the sheath, removal from the lumen of the tubular body or an opening of the shaft, or may be manipulable at their proximal ends for opening and closing the hoops. The tissue removal device may include one or more hoops, rings or any other flexible structure, including inflatable structures, or combinations thereof. All such changes and modifications are intended to be included within the scope of the disclosure.

What is claimed is:

1. A tissue removal device, comprising:
a tubular body defining a central longitudinal axis having a distal end, a proximal end, and defining a lumen at least partially therethrough, the tubular body including discrete first and second longitudinal portions extending in parallel relation to the central longitudinal axis such that the first and second portions are radially separated, the first and second portions being configured and dimensioned for releasable connection such that the first portion and the second portion are completely detachable, wherein one of the first and second portions of the tubular body includes graspers coupled thereto configured and dimensioned to engage tissue;
a bag support structure configured and dimensioned for positioning within the tubular body; and
a bag operatively coupled to the bag support structure and including a first end portion defining an open end, a mid-portion, and a second end portion opposite the first end portion, wherein the bag support structure is movable between a first configuration, wherein the bag support structure is configured and dimensioned for positioning within the tubular body, and a second configuration, wherein the bag support structure is configured and dimensioned to open the bag, the bag support structure further including a first member disposed between the first end portion and the second end portion for at least partially closing the bag.

2. The tissue removal device of claim 1, wherein the first member comprises a ring operatively connected to a distal end of a rod.

3. The tissue removal device according to claim 1, wherein the first member comprises a first hoop operatively connected to the bag at a location spaced a distance from the first end portion of the bag.

4. The tissue removal device as in claim 3, wherein the bag support structure further includes a second member spaced laterally from the first member, the second member including a respective hoop, wherein each of the hoops of the first and second members are movable between a first configuration, wherein the bag is closed, and a second configuration, wherein the bag is open.

5. The tissue removal device as in claim 4, wherein each of the hoops of the first and second members is made of a wire extending through at least one aperture formed in the distal end of the tubular body, wherein displacement of the wire of each of the hoops of the first and second members, in a distal direction, urges the respective one of the hoops of the first and second members to the second configuration, and wherein displacement of the wire of each of the hoops of the first and second members, in a proximal direction, urges the respective one of the hoops of the first and second members to the first configuration.

6. The tissue removal device according to claim 2, wherein the ring is operatively connected to the first end portion of the bag, and wherein a hoop is operatively connected to the bag at a location spaced a distance from the first end portion of the bag.

7. The tissue removal device according to claim 2, wherein the ring is formed from a resilient material, the ring being movable between a first configuration, wherein the ring is biased for positioning within the tubular body, and a second configuration, wherein the ring is unbiased, and defines a diameter larger than an inner diameter of the tubular body.

8. The tissue removal device according to claim 1, wherein a mid-portion of the bag defines a first diameter, and the first end portion of the bag defines a second diameter which is greater than the first diameter of the mid-portion.

9. The tissue removal device according to claim 1, further comprising a removable sheath encasing the bag and the distal end of the bag support structure therein.

10. The tissue removal device according to claim 1, further comprising a plurality of ribs extending longitudinally along a length of the bag.

11. The tissue removal device according to claim 1, wherein the first portion of the tubular body includes a lumen extending therethrough, and the second portion of the tubular body includes a lumen extending therethrough.

12. The tissue removal device according to claim 11, wherein the bag support structure further includes a second member spaced laterally from the first member.

13. The tissue removal device according to claim 12, wherein the first member is movable through the lumen of the first portion of the tubular body, and the second member is movable through the lumen of the second portion of the tubular body, the first member being actively controlled independently of the second member.

14. The tissue removal device according to claim 13, further including a control portion at least partially positioned proximally of the bag support structure, the first member and the second member being operatively connected to the control portion.

15. A tissue removal device, comprising:
a tubular body defining a longitudinal axis having a proximal end, a distal operative end, and a cylindrical outer surface divided along a plane extending in parallel relation to the longitudinal axis to define discrete first and second portions of the tubular body, wherein the first and second portions of the tubular body are positioned in adjacent relation such that the first and second portions extend along substantially parallel axes in radially spaced relation, the first and second portions of the tubular body being configured and dimensioned for releasable connection to allow for modification of the operative end of the tubular body via replacement of at least one of the first and second portions to enable the tissue removal device to perform various surgical functions;

a bag support structure connected to at least one of the first and second portions of the tubular body, the bag support structure including proximal and distal ends, and first and second members extending through the tubular body; and a bag operatively coupled to the bag support structure, the bag including a first open end and a second closed end, wherein the bag support structure is repositionable between first and second positions upon movement of the first and second members through the tubular body, wherein the bag is configured, dimensioned, and positioned to receive tissue when the bag support structure is in the first position, and the bag is configured, dimensioned, and positioned to prevent tissue from entering an interior portion of the bag when the bag support structure is in the second position.

16. The tissue removal device of claim 15, wherein the first member of the bag support structure is positioned between the open end of the bag and the closed end of the bag, and the second member of the bag support structure is spaced laterally from the first member of the bag support structure.

17. The tissue removal device according to claim 15, wherein the first member of the bag support structure includes a hoop operatively connected to the bag at a first location, the hoop extending from the first portion of the tubular body, and the second member of the bag support structure includes a hoop operatively connected to the bag at a second location longitudinally spaced from the first location, the hoop of the second support structure extending from the second portion of the tubular body.

18. The tissue removal device according to claim 17, wherein the first portion of the tubular body includes a first lumen extending therethrough, and the second portion of the tubular body includes a second lumen extending therethrough.

19. The tissue removal device according to claim 18, wherein the first member of the bag support structure is configured and dimensioned for movement through the first lumen of the first portion of the tubular body, and the second member of the bag support structure is configured and dimensioned for movement through the second lumen of the second portion of the tubular body.

20. The tissue removal device as in claim 19, wherein each of the hoops of the first and second support structures is made of a wire extending at least partially through the lumen of the first or second portion of the tubular body and distally beyond the distal end of the tubular body, wherein distal displacement of the wire of each of the hoops of the first and second support structures through the lumen of a respective first and second portion of the tubular body facilitates movement of the bag support structure into the first position, and proximal displacement of the wire of each of the hoops of the first and second support structures through the lumen of the respective tubular body facilitates movement of the bag structure into the second position.

21. The tissue removal device of claim 15, further including a control portion at least partially positioned proximally of the bag support structure, the first and second members of the bag support structure being operatively connected to the control portion such that the first member is actively controlled independently of the second member via the control portion to facilitate repositioning of the bag support structure between the first and second positions.

22. The tissue removal device of claim 15, wherein one of the first and second portions of the tubular body supports graspers coupled thereto configured and dimensioned to engage tissue.

23. The tissue removal device of claim 15, wherein the second member of the bag support structure includes a rod having proximal and distal ends, and a ring operatively connected to the distal end of the rod, the bag being connected to the ring.

24. The tissue removal device according to claim 15, further comprising a removable sheath configured and dimensioned to encase the bag and the distal end of the bag support structure.

25. A tissue removal device, comprising:

a tubular body defining a longitudinal axis having a proximal end, a distal operative end, and a cylindrical outer surface divided along a plane extending in parallel relation to the longitudinal axis to define discrete first and second portions of the tubular body, wherein the first and second portions of the tubular body are positioned in adjacent relation such that the first and second portions extend along substantially parallel axes in radially spaced relation, the first and second portions of the tubular body being configured and dimensioned for releasable connection to allow for modification of the operative end of the tubular body via replacement of at least one of the first and second portions to enable the tissue removal device to perform various surgical functions; and tissue receiving structure positioned adjacent the operative end of the tubular body, the tissue receiving structure being repositionable between an open position, wherein the tissue receiving structure is configured, dimensioned, and positioned to receive tissue, and a closed position, wherein the tissue receiving structure is configured, dimensioned, and positioned to prevent tissue from entering an interior portion of the tissue receiving structure.

26. The tissue removal device according to claim 25, wherein the tissue receiving structure includes a bag support structure connected to at least one of the first and second portions of the tubular body, the bag support structure first and second members extending through the tubular body.

27. The tissue removal device according to claim 26, wherein the tissue receiving structure further includes a bag operatively coupled to the bag support structure.

28. The tissue removal device according to claim 27, wherein the bag support structure is repositionable upon movement of the first and second members through the tubular body to reconfigure the bag and facilitate receipt of tissue within the bag.

29. The tissue removal device according to claim 1, wherein the tubular body includes a cylindrical outer surface divided along a plane extending in parallel relation to the central longitudinal axis to define the first and second portions of the tubular body.

* * * * *